(12) United States Patent
Demuth et al.

(10) Patent No.: US 6,319,893 B1
(45) Date of Patent: Nov. 20, 2001

(54) RAISING BLOOD SUGAR LEVEL IN HYPOGLYCEMIC MAMMALS BY ADMINISTERING INHIBITORS OF DIPEPTIDYL PEPTIDASE IV

(75) Inventors: Hans-Ulrich Demuth; Torsten Hoffmann; Kerstin Kuhn-Wache; Fred Rosche, all of Halle/Saale (DE)

(73) Assignee: Probiodrug, Halle (DE)

( * ) Notice: Subject to any disclaimer, the term of this patent is extended or adjusted under 35 U.S.C. 154(b) by 0 days.

(21) Appl. No.: 09/365,404

(22) Filed: Aug. 2, 1999

(30) Foreign Application Priority Data

Jul. 31, 1998 (DE) .............................. 198 34 591

(51) Int. Cl.$^7$ .......................... A01N 37/18; A61K 38/00; A61K 38/26; A61K 39/395

(52) U.S. Cl. .............................. 514/2; 424/130.1; 514/19

(58) Field of Search ............................. 424/94.63, 130.1; 514/2, 19

(56) References Cited

U.S. PATENT DOCUMENTS

| | | | |
|---|---|---|---|
| 2,961,377 | 11/1960 | Shapiro et al. | 514/635 |
| 3,960,949 | 6/1976 | Ahrens et al. | 564/233 |
| 4,935,493 | * 6/1990 | Bachovchin et al. | 530/331 |
| 5,433,955 | 7/1995 | Bredehorst et al. | 424/94.3 |
| 5,512,549 | * 4/1996 | Chen et al. | 514/12 |
| 5,614,379 | 3/1997 | MacKellar | 435/68.1 |
| 5,624,894 | 4/1997 | Bodor | 514/2 |
| 6,006,753 | * 12/1999 | Efendic | 128/898 |

FOREIGN PATENT DOCUMENTS

| | | |
|---|---|---|
| 296 075 | 11/1991 | (DD) . |
| 25 42598 A1 | 10/1974 | (DE) . |
| 19616486 | 10/1997 | (DE) . |
| 0 658 568 A1 | 12/1994 | (EP) . |
| 0 708 179 A2 | 10/1995 | (EP) . |
| 2085665 | 3/1971 | (FR) . |
| 2696740 | 10/1992 | (FR) . |
| 4334357 A2 | 11/1992 | (JP) . |
| WO 93/08259 A2 | 4/1993 | (WO) . |
| WO 95/11689 | 5/1995 | (WO) . |
| WO 95/15309 | 6/1995 | (WO) . |
| WO 95/29691 | 11/1995 | (WO) . |
| WO 97/40832 | 11/1997 | (WO) . |
| WO 97/45117 | 12/1997 | (WO) . |
| WO 98/22494 | 5/1998 | (WO) . |
| WO 00/53171 | 9/2000 | (WO) . |

OTHER PUBLICATIONS

Campbell, I.W., Sulphonylureas and metformin: efficacy and inadequacy. 3:33–51 (1990).

Merck Index, 11$^{th}$ Edition, p. 934, 1989.

Martindale the Extra, Pharmacopoeia, p. 1619, 1996.

J. Lin et al.: "Inhibition of depeptidyl peptidase IV by fluoroolefin-containing n-peptidyl-O-hydroxylamine peptidomimetics" Proceedings of the National Academy of Sciences of USA, vol. 95, Nov. 1998 pp. 14020–14024.

Korom, S. et al., Inhibition of CD26/dipeptidyl peptidase IV activity in vivo prolongs cardiac allograft survival in rat recipients, Transplantation vol. 63, pp. 1495–1500, No. 10, May 27, 1997.

Tanaka, S. et al., Suppression of arthritis by the inhibitors of dipeptidyl peptidase IV. Int. J. Immunopharmacol. vol. 19, No. 1, pp. 15–24 (1997).

Mentlein, R. et al, Proteolytic processing of neuropeptide Y and peptide YY by dipeptidyl peptidase IV. Regul. Pept. 49, (1993) 133–144.

Wetzl, W. et al., Effects of the CLIP fragment ACTH 20–24 on the duration of REM sleep episodes, Neuropeptides, 31, (1), pp. 41–45 (1997).

Wakselman, M. et al., Inhibition of HIV–1 infection of CD 26+ *but not CD26−* cells by a potent cyclopeptidic inhibitor of the DPP IV activity of CD 26. Abstract P 44 of the 24th European Peptide Symposium 1996.

Willms, B. et al., Gastric Emptying, Glucose Response, and Insulin Secretion after a Liquid Test Meal: Effects of Exogenous Glucagon–Like Peptide–1 (GLP–1)–(7–36) Amide in Type 2 (Noninsulin–Dependent) Diabetic Patients. *JCEM* 81:327–332 (1996) No. 1.

Arai, H. et al: "Synthesis of proplyl endopeptidase inhibitors and evaluation of their structure–activity relationships : in vitro inhibition of prolyl endopeptidase from canine brain" Chemical and Pharmaceutical Bulletin., vol. 41, Nr. 9, 1993, pp. 1583–1588.

Amasheh, S. et al., Electrophsiological analysis of the function of the mammalian renal peptide transporter expressed in *Xenopus Laevis oocytes*. J. Physiol. 504, 169–174 (1997).

Chemical Abstracts, vol. 115. No. 15, Oct. 14, 1991 Columbus, Ohio, US; abstract No. 149947q, Schoen Ekkehard et al: "Dipeptidyl peptidase IV in the immune system.Effects of specific enzyme inhibitors on activity of dipeptidyl peptidase IV and proliferation of human lymhocytes" Seite 37; XP002114197 Zusammenfassung & Biol. Chem. Hoppe–Seyler, Bd. 372, Nr. 5, 1991, Seiten 305–311.

(List continued on next page.)

Primary Examiner—David M. Naff
Assistant Examiner—Mike Meller
(74) Attorney, Agent, or Firm—Mark A. Hofer; Brown, Rudnick, Freed & Gesmer

(57) ABSTRACT

A method of raising the blood sugar level in a mammal having hypoglycemia is described. The method reduces degradation of glucagon by administering to the mammal a therapeutically effective amount of an inhibitor of dipeptidyl peptidase IV and physiologically acceptable adjuvants and/or excipients.

4 Claims, 4 Drawing Sheets

OTHER PUBLICATIONS

Chemical Abstracts, vol. 126, No. 2, Jan. 13, 1997 Columbus, Ohio, US; abstract No. 16161j, Stoeckel A. et al: "Competetive inhibition of proline specific enzymes by amino acid thioxopyrrolidides and thiazolidides" Seite 241; XP002114198 Zusammenfassung & Pept: Chem., Struct.Biol., Proc.Am.Pept.Symp., Nr. 14, 1995, Seiten 709–710.

Chemical Abstracts, vol. 118, No. 25, Jun. 21, 1993, Columbus, Ohio, US; abstract No. 255342k, Seite 933; XP002114199 Zusammenfassung & JP 040 334357 A (Fujerebio Inc) Nov. 20, 1992.

Thorens, B et al., Glucagon–Like Peptide–I and the Control of Insulin Secretion in the Normal State and in NIDDM. *Diabetes* 42:1219–1225 (1993).

Orskov C. et al., Proglucagon Products in Plasma of Non-insulin–dependent Diabetics and Nondiabetic Controls in the Fasting State and After Oral Glucose and Intravenous Arginine. *J. Clin. Invest.* 87:415–423 (1991).

Pauly, R. et al., Improved Glucose Tolerance in Rats Treated with the Dipeptidyl Peptidase IV (CD26) Inhibitor ILE–Thiazolidide. *Metabolism* 48:385–389 (1999).

Winslow, R., Novartis Drug Alters Picture for Diabetes. *Wall Street Journall*, Wed. Dec. 27, 2000, p. B2.

Hendrick, G.K. et al., Glucagon–Like Peptide–I–(7–37) Suppresses Hyperglycemia in Rats. *Metabolism* vol. 42, No. 1, pp. 1–6 (Jan. 1993).

Deacon, C. et al., Degradation of Glucagon–Like Peptide–1 by Human Plasma in Vitro yields an N–Terminally Truncated Peptide that is a Major Endogenous Metabolite in Vivo. *JCEM* 80:952–957, (Apr. 25, 1995).

Hoffman, T. et al., Inhibition of Dipeptidyl Peptidase IV (DPIV) by anti–DP IV antibodies and non–substrate X–X–Pro– Oligopeptides Ascertained by Capillary Electrophoresis. *Journal of Chromatography A*, 716 335–362 (1995).

Nauck, M.A. et al., Normalization of Fasting Hyperglycaemia by Exogenous Glucagon–Like Peptide 1 (7–36 Amide) in Type 2 (Non–insulin–dependent) Diabetic Patients. *Diabetologia* 36:741–744 (1993).

Gutniak, M.K. et al., Subcutaneous Injection of the Incretin Hormone Glucagon–Like Peptide 1 Abolishes Postprandial Glycemia in NIDDM. *Diabetes Care* 17:1039–1044, (Sep. 1994).

\* cited by examiner

RAISING BLOOD SUGAR LEVEL IN HYPOGLYCEMIC MAMMALS BY ADMINISTERING INHIBITORS OF DIPEPTIDYL PEPTIDASE IV

The invention relates to a method in which, by reducing dipeptidyl peptidase IV (DP IV) or DP IV-analogous enzyme activity in the blood of a mammal by administration of activity-reducing effectors, the endogenous (or additionally exogenously administered) glycogenolytically active peptide glucagon or analogues thereof is/are degraded to a reduced extent by DP IV and DP IV-like enzymes, thereby reducing or delaying the decrease in concentration of that peptide hormone or analogues thereof.

Owing to that increased stability of (endogenous or exogenously administered) glucagon and its analogues brought about by the action of DP IV effectors, thereby making them available in greater number for the glycogenolytic stimulation of the glucagon receptors of, in particular, liver cells, the duration of activity of the body's own glucagon changes, consequently resulting in stimulation of the catabolic carbohydrate metabolism of the organism treated.

As a result, the blood sugar level in the serum of the treated organism rises above the glucose concentration characteristic of hypoglycaemia. Thereby, metabolic anomalies, such as hypoglycaemic states resulting from reduced glucose concentrations in the blood, can be prevented or alleviated.

In addition to proteases involved in non-specific proteolysis, which ultimately causes the degradation of proteins into amino acids, regulatory proteases are known which take part in the functionalisation (activation, deactivation, modulation) of endogenous peptide active substances (Kirschke et al., 1995; Kräusslich & Wimmer, 1987). Especially in connection with immune research and neuropeptide research, a number of such so-called convertases, signal peptidases or enkephalinases have been discovered (Gomez et al., 1988; Ansorge et al., 1991).

In view of the frequency with which the amino acid proline occurs in a large number of peptide hormones and the associated structural characteristics of those peptides, a function analogous to that of the signal peptidases is being discussed for proline-specific peptidases (Yaron & Naider, 1993; Walter et al., 1980; Vanhoof et al., 1995). By its special structure, proline in those peptides determines both conformation and stability of those peptides by protecting them from being degraded by non-specific proteases (Kessler, 1982).

Enzymes that have a highly specific structure-altering effect on proline-containing sequences (HIV protease, cyclophilin etc.) are attractive targets for current active substance research. In particular for the peptidases prolyl endopeptidase (PEP) and dipeptidyl peptidase IV (DP IV) which cleave after the proline, relationships between modulation of the biological activity of natural peptide substrates and their selective cleavage by those enzymes could be made plausible. Thus, it is assumed that PEP plays a role in learning and in the memory process and that DP IV is involved in signal transmission during the immune response (Ishiura et al., 1990; Hegen et al., 1990).

As with the extraordinary proline specificity of those enzymes, there is discussion about their high selectivity for the amino acid alanine inside typical recognition regions in substrates of those enzymes, according to which alanine-containing peptides can adopt similar conformations to the structurally analogous proline-containing peptides. Such properties of alanine-containing peptide chains have recently been demonstrated by point mutation (exchange of proline for alanine) (Dodge & Scheraga, 1996).

DP IV and DP IV-analogous activity (for example cytosolic DP II has a substrate specificity virtually identical to that of DP IV) occurs in the blood circulation where it removes dipeptides from the N-terminus of biologically active peptides in a highly specific manner when proline or alanine form the adjacent residues of the N-terminal amino acid in their sequence. On the basis of that cleavage site specificity, it is assumed that that enzyme and analogues are involved in the regulation of polypeptides in vivo (Vanhoof et al., 1995).

Blood sugar concentrations that are too low may lead to pathological states in the human or animal organism. In particular, after accidents, so-called hypoglycaemic shock may occur which may lead in patients to hyperorexia, sweating and even to loss of consciousness and death.

It was therefore a problem of the present invention to provide agents for preventing or alleviating pathological metabolic anomalies of mammalian organisms, such as acute or chronic hypoglycaemia.

In particular, it was a problem of the present invention to provide agents by means of which carbohydrate reserves, for example of the liver, can be rapidly mobilised.

Those problems are solved according to the invention by the use of activity-reducing effectors of dipeptidyl peptidase IV (DP IV) and DP IV-analogous enzyme activity to raise the blood sugar level in a mammalian organism.

It is already known to use activity-reducing effectors of DP IV to lower the blood sugar level of mammalian organisms. In so doing, the degradation of incretins, which stimulate glucose disposal, by DP IV is stopped.

It is therefore especially surprising that activity-reducing effectors of DP IV and DP IV-analogous enzyme activity can be used to raise the blood sugar level. Presumably, that effect relies on the following mechanisms:

In glucose metabolism and catabolism in the human and animal body, a distinction can be made in principle between two phases:

1. In the first phase, following food intake, increased release of incretins takes place (i.e. hormones that stimulate insulin secretion of the pancreas, such as gastric inhibitory polypeptide 1-42 ($GIP_{1-42}$) and glucagon-like peptide amide-1 7-36 ($GLP-1_{7-36}$)), resulting in increased insulin production and, as a consequence, in increased degradation of the glucose supplied by food intake.

Incretins are, however, substrates of DP IV, since the latter is able to remove the dipeptides tyrosinyl alanine and histidyl alanine from the N-terminal sequences of incretins in vitro and in situ (Mentlein et al., 1993). Consequently, if DP IV is present, degradation of the incretins occurs, which in turn leads to reduced glucose disposal.

By inhibiting the DP IV and DP IV-analogous enzyme activity in vivo, therefore, it is possible effectively to suppress excessive degradation of the incretins and consequently to increase glucose disposal:

DP IV inhibition leads to stabilisation of the incretins, the extended life of the incretins in the blood circulation intensifies their insulinotropic and insulin-sensitising action, the consequently increased and more effective insulin release brings with it an increased glucose tolerance (Demuth et al., 1996).

It has been demonstrated in diabetic rats that the corresponding DP IV inhibitors can be used effectively to modulate the control system described (Pederson et al., 1998). That phase lasts approximately 120 minutes from the time of food intake.

After that so-called postprandial phase has elapsed, the secretion of incretins is stopped and any already existing incretins are degraded by DP IV. As a result, insulin production falls, bringing glucose disposal to an end.

2. In order to maintain the physiologically necessary glucose concentration of approximately 5.5 mmol/l between food intakes, in the second phase stored glycogen is degraded, for which glucagon is released from the pancreatic A-cells. Glucagon has, therefore, an opposite effect to insulin and hence also to the incretins.

In the case of three meals a day, the human body is accordingly under GLP-1/GIP and insulin control for approximately 6 hours (3×120 minutes), but under glucagon control for 18 hours.

It has been established that DP IV is endogenously released from the same secretory granules of the A-cells as glucagon and that that release may take place simultaneously with the release of glucagon and the onset of glucagon action. According to the invention, it has now been found that glucagon both in vitro and in vivo is degraded and thereby deactivated by DP IV and DP IV-analogous enzyme activity, see FIG. 1, as a result of which the release of glycogen and consequently of glucose is retarded or stopped. That fact was completely surprising, since it had previously been assumed that, as mentioned above, DP IV causes only lowering of the blood sugar level.

The possibility therefore presents itself, according to the invention, of promoting the release of endogenous stored glucose from glycogen by means of glucagon by influencing DP IV activity and analogous activities; simultaneous stimulation of glucose disposal does not occur, since no incretins are secreted in the human organism approximately 2 hours after meals.

The invention is based, therefore, on the surprising discovery that a reduction of the DP IV or DP IV-like enzyme activity taking place in the blood circulation leads causally to influencing of the blood sugar level. It has been found that 1. reduction of DP IV and DP IV-analogous activity results in increased stability of externally supplied or endogenously circulating glucagon, that is to say, by administering effectors of DP IV and DP IV-analogous proteins, glucagon degradation in the blood can be controlled;

2. by increasing the stability of endogenously circulating or externally supplied glucagon, a controllable modulation of the blood glucose level occurs.

The invention accordingly relates to the use of effectors of dipeptidyl peptidase IV (DP IV) and DP IV-analogous enzyme activity to raise the blood sugar level in the serum of a mammalian organism above the glucose concentration characteristic of hypoglycaemia.

The invention relates especially to the use and administration of effectors of DP IV and DP IV-analogous enzyme activity in and to mammals for the prevention or alleviation of pathological metabolic anomalies of mammalian organisms. Such an anomaly may be, for example, acute or chronic hypoglycaemia where rapid mobilisation of carbohydrate reserves of the liver is necessary.

In another preferred embodiment, the invention relates to use and a method for raising the blood sugar level in the serum of a mammalian organism above the glucose concentration characteristic of hypoglycaemia. For that purpose, a therapeutically effective amount of an effector of DP IV and DP IV-analogous enzyme activity may be administered to a mammalian organism.

A significant advantage of the present invention is the low burden imposed on the organism, since only small doses of external hormone, if any, need to be administered: according to the invention, glucagon degradation is decelerated or completely stopped by the use of the DP IV inhibitors of the invention, so that, in the organism of an adult human, typically a quantity of administered or endogenously released glucagon of from 2 pmol to 200 pmol is maintained. Too rapid a proteolytic degradation is prevented.

The effectors of DP IV and DP IV-analogous enzymes administered according to the invention may be used in pharmaceutically administrable formulation complexes as inhibitors, substrates, pseudosubstrates, inhibitors of DP IV expression, binding proteins or antibodies to those enzyme proteins or combinations of those different substances that reduce the DP IV or DP IV-analogous protein concentration in the mammalian organism. Effectors used according to the invention are, for example, DP IV inhibitors, such as the dipeptide derivatives and dipeptide mimetics alanyl-pyrolidine, isoleucyl-thiazolidine, and the pseudosubstrate N-valyl-prolyl, O-benzoyl hydroxylamine or salts thereof, especially fumarates thereof. Such compounds are known from the literature or can be manufactured analogously to the methods described in the literature (Demuth, 1990).

The method of the invention represents a novel procedure for raising lowered blood glucose concentration in the serum of mammals. It is simple, capable of commercial exploitation and suitable for use in human medicine in the treatment especially of diseases that result from below-average blood glucose values.

The effectors may be used in the form of pharmaceutical preparations that contain the active ingredient in combination with customary excipients known from the prior art and/or customary adjuvants. They are administered, for example, parenterally (for example i.v., in physiological saline solution) or enterally (for example orally, formulated with customary excipients such as, for example, glucose).

Depending upon their endogenous stability and bio-availability and upon the severity of the condition, single or multiple doses of the effectors may be administered to obtain the desired normalisation of the blood glucose values. For example, in the case of aminoacyl-thiazolidines, such a dosage range may he from 0.1 mg to 10 mg of effector substance per kilogram. The effectors are preferably administered approximately 120 minutes after food intake. The effectors may also be used together with or at short intervals from glucagon or analogues thereof.

EXAMPLE 1

Figure 1:
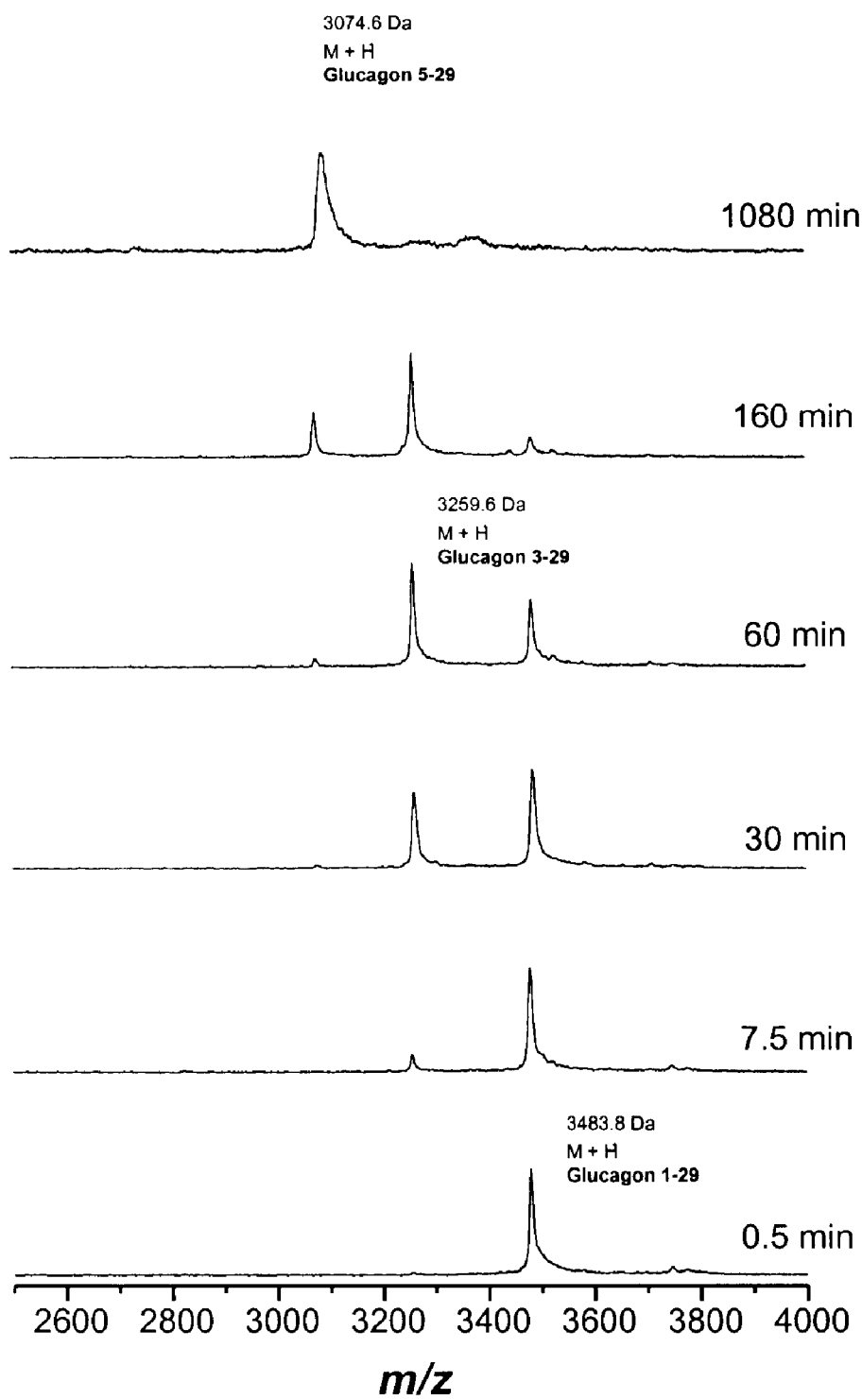
FIG. 1 shows MALDI-TOF Mass Spectra of 0.14 mmol Glucagon Solution and 40 mmol TRIS/HCL (pH=7.6) in the presence of 40 nmol DP IV (the removal of the dipeptides His-Ser and Gln-Gly occurs sequentially depending upon the incubation time)
Figure 2:
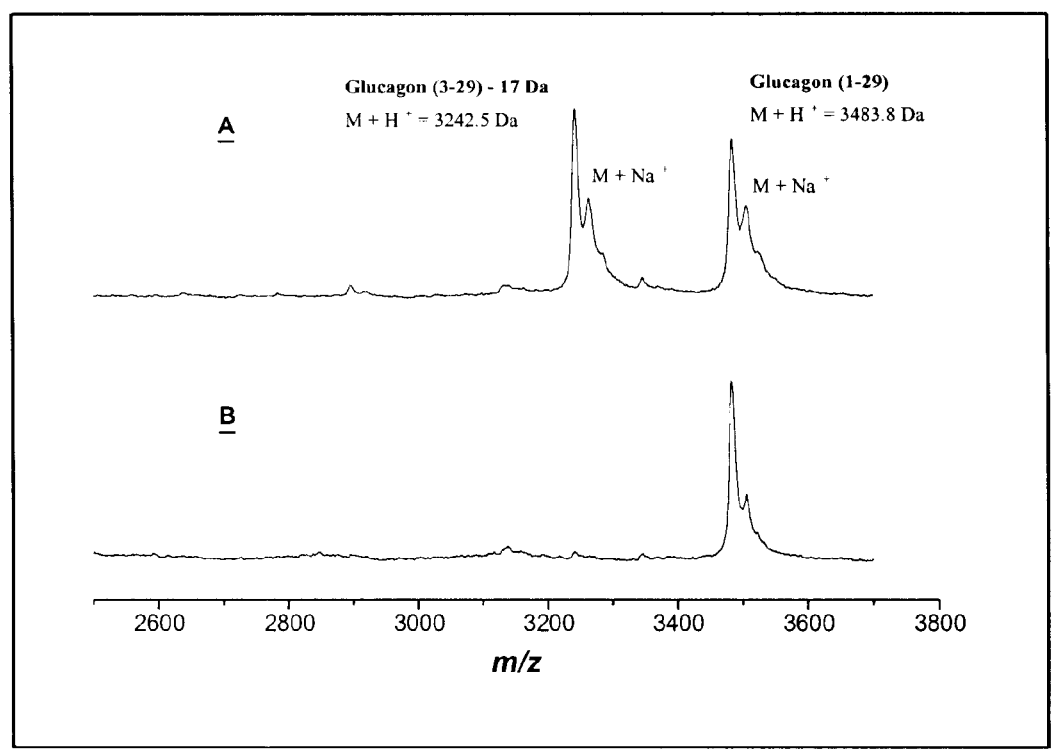
FIG. 2 shows MALDI-TOF mass spectra of a glucagon-scrum mixture; A-serum-DP IV hydrolyses glucagoni, B-suppression of DP IV catalyzed glucagoni hydrolysis by the DP IV inhibitor, isolcucylthiazolidine.

Inhibition of Serum DP IV-catalysed Glucagon Cleavage by the DP IV Inhibitor Isoleticyl-thiazolidine See FIG. 1

EXAMPLE 2

Figure 3:
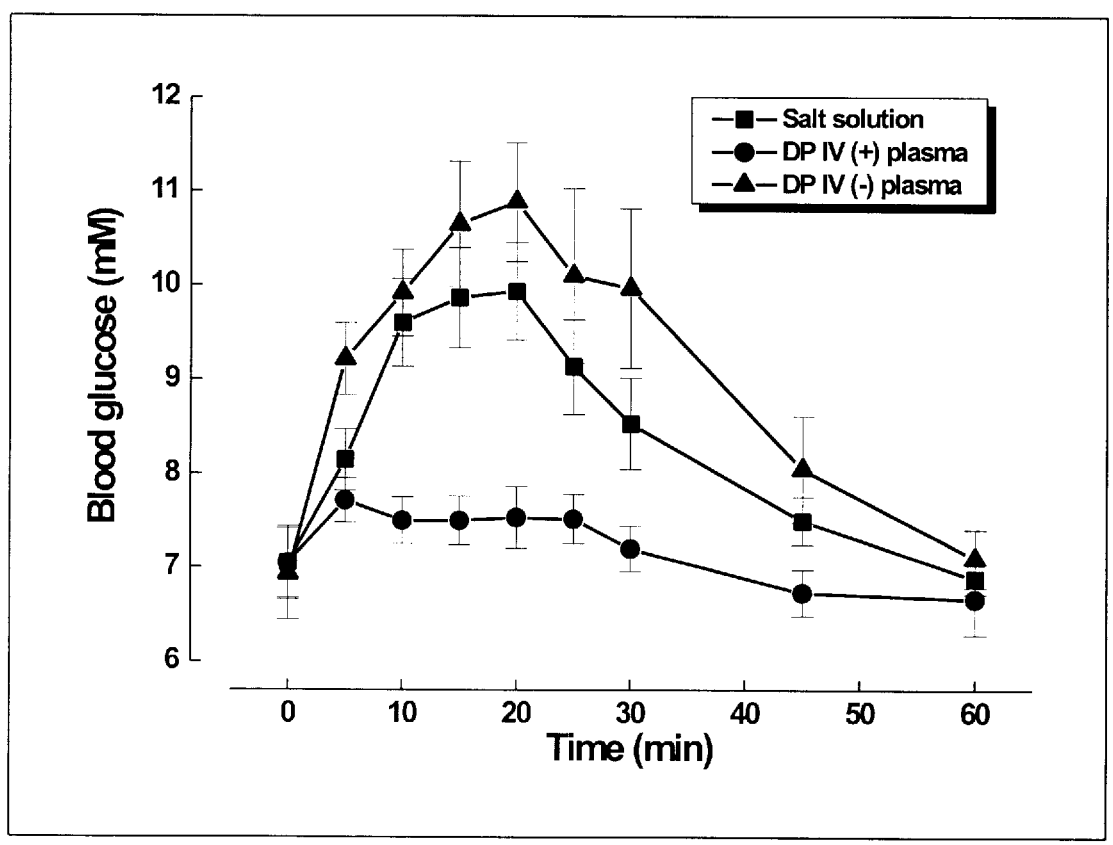
FIG. 3 shows the effect of glucagon on cendogenous glucose release in Wistar rats after i.v. injection of glucagon, pre-incubated in plasma of DP IV-positive and DP IV-negative rats.

Effect of Glucagon on Endogenous Glucose Release After Incubation in Plasma of DP IV-positive and DP IV-negative Rats To test whether glucagon-degrading activity is present in the plasma of DP IV-negative rats, 6.8 µg of glucagon were preincubated for three hours at 37° C. in 1.0 ml of plasma of normal, DP IV-positive rats and in 1.0 ml of plasma of DP IV-negative rats. From 10 to 50 µl of the incubation solution were injected i.v. into normal Wistar rats and compared with a saline control. The biological response, that is to say the increase in blood glucose resulting from the glucagon-stimulated release of hepatic glucose, was monitored for 60 minutes (FIG. 3).

EXAMPLE 3

Figure 4:
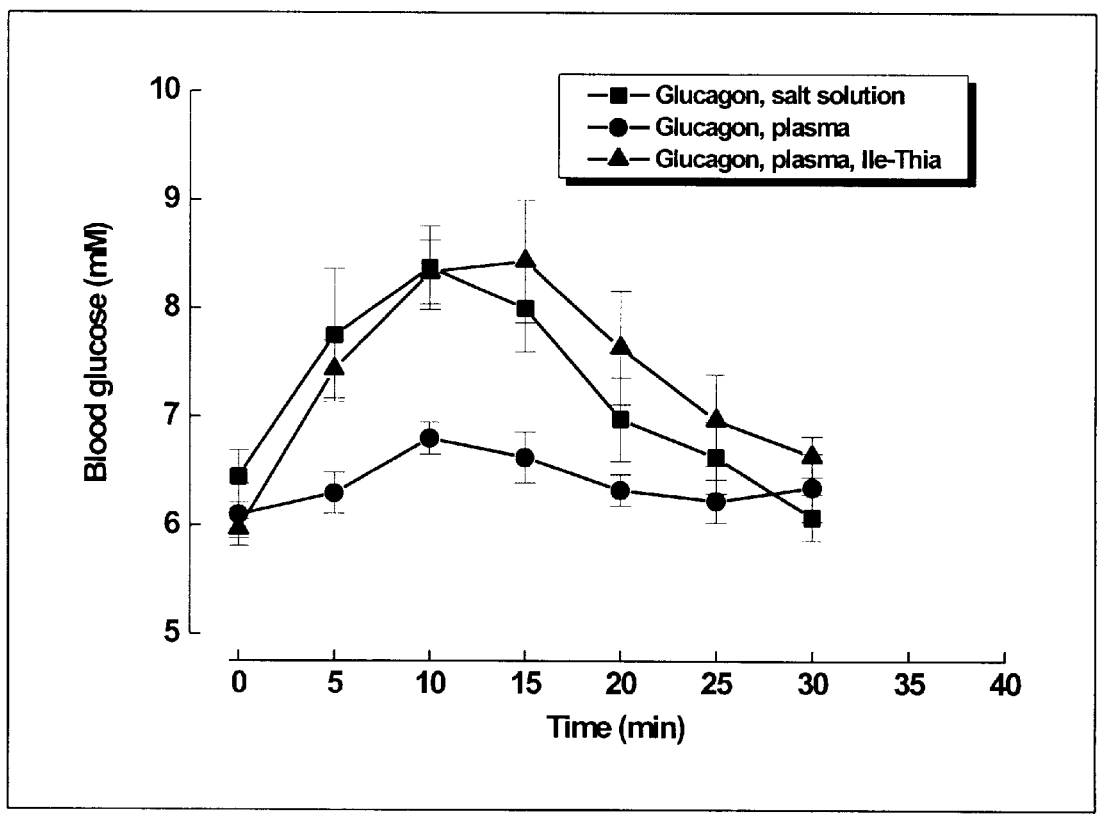
FIG. 4 shows the effect of glucagoni on cendogenous glucose release in Wistar rats after i.v. injection of glucagon, pre-incubated in plasma of normal rats, in the presence of absence of specific DP IV-inhibitor.

Effect of Glucagon on Glucose Response in Wistar Rats after i.v. Injection of Preincubated Glucagon in the Plasma of a Normal Rat, in the Presence and Absence of DP IV Inhibitor To test whether the effect of the glucagon-degrading activity in plasma can be inhibited by a specific DP IV inhibitor, 6.8 µg of glucagon were induced for three hours at 37° C. in 1.0 ml of normal rat plasma and in 1.0 ml of normal rat plasma additionally containing 0.01 mmol of isoleucyl-thiazolidine. From 10 to 50 µl of the incubation solution were injected i.v. into normal Wistar rats and compared with a saline control. The biological response, that is to say the increase in blood glucose resulting from the glucagon-stimulated release of hepatic glucose, was monitored for 30 minutes (FIG. 4).

BIBLIOGRAPHY

Ansorge, S., Schön, E., and Kunz, D. (1991). Membrane-bound peptidases of lymphocytes: functional implications. *Biomed. Biochim.* Acta 50, 799–807.

Demuth, H. -U. (1990) Recent developments in the irreversible inhibition of serine and cysteine proteases. *J. Enzyme Inhibition* 3, 249–280.

Demuth, H. -U., Rosche, F., Schmidt, J., Pauly, R. P., McIntosh, C. H. S. and Pederson, R. A. (1996). Verfahren zur Steigerung des Blutglukosespiegels in Säugern. DE 196 16 486.

Dodge, R. W. & Scheraga, H. A. (1996). Folding and unfolding kinetics of the proline-to-alanine mutants of bovine pancreatic ribonuclease A. *Biochemistry* 35, 1548–1559.

Gomez, S., Gluschankof, P., Lepage, A., and Cohen, P. (1988). Relationship between endo-and exopeptidases in a processing enzyme system: activation of an endoprotease by the aminopeptidase B-like activity in somatostatin-28 convertase. *Proc Natl Acad Sci USA* 85, 5468–5472.

Hegen, M., Niedobitek, G., Klein, C. E., Stein, H., and Fleischer, B. (1990). The T cell triggering molecule Tp 103 is associated with dipeptidyl aminopeptidase IV activity. *J. Immunology* 144, 2908–2914.

Ishiura, S., Tsukahara, T., Tabira, T., Shimuzu, T., Arahata, K., and Sugita H. (1990). Identification of a putative amyloid A4-generating enzyme as a prolyl endopeptidase *FEBS-Letters* 260, 131–134.

Kräusslich, H. -G. and Wimmer, E. (1987). Viral Proteinases. *Ann. Rev. Biochem.* 57, 701

Kessler, H. (1982). Konformation und biologische Wirkung von zyklischen Peptiden. *Angew. Chem.* 94, 509–520.

Mentlein, R., Gallwitz, B., and Schmidt, W. E. (1993). Dipeptidyl Peptidase IV hydrolyzes gastric inhibitory polypeptide, glucagon-like peptide-1(7-36)amide, peptide histidine methionine and is responsible for their degradation in human serum. *Eur. J. Biochem.* 214, 829–835.

Pederson, R. A., White, H. A., Schlenzig, D., Pauly, R. P., McIntosh, C. H. S., and Demuth, H. -U. (1998). Improved glucose tolerance in zucker fatty rats treated by oral administration of the dipeptidyl peptidase IV inhibitor isoleucyl thiazolidine. *Diabetes* 47, 1253–1258.

Vanhoof, G., Goossens, F., De Meester, I., Hendriks, D., and Scharp, S. (1995). Proline motifs and their biological processing. *FASEB Journal* 9, 736–744.

Walter, R., Simmons, W. H., and Yoshimoto, T. (1980). Proline Specific Endo- and Exopeptidases. *Mol. Cell. Biochem.* 30, 111–127.

Yaron, A. and Naider, F. (1993). Proline-dependent structural and biological properties of peptides and proteins. *Crit. Rev. Biochem. Mol. Biol.* 28(1), 31–38.

Kirschke, H., Barrett, A. J., Rawlings, N. D. (1995). Proteinases 1: Lysosomal cysteine proteinases. Protein profile 2/14, pp. 1581–1634

What is claimed is:

1. A method of raising the blood sugar level in a mammal having hypoglycemia by reducing degradation of glucagon, said method comprising administering to said mammal a therapeutically effective amount of an inhibitor of dipeptidyl peptidase (DP IV) and physiologically acceptable adjuvants and/or excipients for reducing in said mammal activity of endogenous DP IV.

2. The method of claim 1, wherein the inhibitor is selected from the group consisting of dipeptide derivative inhibitors of DP IV, substrates of DP IV, pseudosubstrates of DP IV, proteins that bind DP IV, antibodies to DP IV and combinations thereof.

3. The method of claim 1, wherein the inhibitor is employed together with glucagon or analogues thereof.

4. A method for stimulating endogenous glucose production via glucagon stabilization in a mammal having hypoglycemia comprising the step of administering, to said mammal a therapeutically effective amount of a dipeptidyl peptidase IV (DP IV) inhibitor and physiologically acceptable adjuvants and/or excipients for reducing in said mammal the enzymatic activity of endogenous DP IV to reduce degradation of glucagon.

* * * * *